US00PP10497P

United States Patent [19]

Verwer

[11] Patent Number: Plant 10,497

[45] Date of Patent: Jul. 14, 1998

54] DAHLIA PLANT NAME 'GALLERY RENOIR'

75] Inventor: Aad Verwer, Lisse, Netherlands

73] Assignee: Gebr. Verwer, Lisse, Netherlands

21] Appl. No.: 815,862

22] Filed: Mar. 12, 1997

51] Int. Cl.[6] ..... A01N 5/00

52] U.S. Cl. ..... Plt./87.8

58] Field of Search ..... Plt./87.8

56] References Cited

U.S. PATENT DOCUMENTS

| | | | |
|---|---|---|---|
| P.P. 7,762 | 1/1992 | Wilms | Plt./87.8 |
| P.P. 8,459 | 11/1993 | Veenstra | Plt./87.8 |
| PP. 10,124 | 11/1997 | Kleinhanns | Plt./87.8 |

OTHER PUBLICATIONS

GTITM UPOV ROM Listing for 'Gallery Renoir' as per PBR DHL 0062 (NL) Mar. 16, 1996.

*Primary Examiner*—James R. Feyrer
*Assistant Examiner*—Kent L. Bell
*Attorney, Agent, or Firm*—C. A. Whealy

[57] ABSTRACT

A distinct cultivar of Dahlia plant named 'Gallery Renoir', characterized by its suitability for potted plants, garden or patio plants, or as cut flowers; upright and spreading, compact and freely branching plant habit; dark green foliage; early and profuse flowering; rapid growth rate; decorative-type inflorescences that are about 11 cm in diameter; pink-colored ray florets; and good postproduction longevity.

1 Drawing Sheet

The present invention relates to a new and distinct cultivar of Dahlia plant, botanically known as Dahlia hybrid and referred to by the cultivar name 'Gallery Renoir'.

The new cultivar is a product of a planned breeding program conducted by the inventor in Lisse, The Netherlands. The objective of the breeding program is to create compact Dahlia cultivars that flower early and profusely with desirable ray floret color and good post-production longevity.

The new cultivar originated from a cross made by the inventor in the summer of 1992, of the nonpatented commercial cultivar 'Tout à Toi' as the female, or seed, parent with the nonpatented commercial cultivar 'Oriental Dream' as the male, or pollen, parent. Compared to plants of the parent cultivars, the new Dahlia is more compact, more freely branching and inflorescences have a different ray floret color.

The cultivar 'Gallery Renoir' was discovered and selected by the inventor as a flowering plant within the progeny of the stated cross in a controlled environment in Lisse, The Netherlands, in 1992. The selection of this plant was based on its compact and freely branching habit, unique ray floret color, floriferousness and good postproduction longevity.

Asexual reproduction of the new cultivar by terminal cuttings taken in a controlled environment in Lisse, The Netherlands, has shown that the unique features of this new Dahlia are stable and reproduced true to type in successive generations.

The cultivar 'Gallery Renoir' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gallery Renoir'. These characteristics in combination distinguish 'Gallery Renoir' as a new and distinct cultivar:

1. Suitable for potted plants, garden or patio plants, or as cut flowers.
2. Upright and spreading, compact and freely branching plant habit.
3. Dark green foliage.
4. Early and profuse flowering.
5. Rapid growth rate.

6. Large decorative-type inflorescences that are about 11 cm in diameter.
7. Pink-colored ray florets.
8. Good postproduction longevity with open inflorescences maintaining good substance and color for about 14 days and plants maintaining good substance and flowering for 3 to 4 months.

The accompanying photograph illustrates the overall appearance of the new cultivar. The colored photograph comprises a side perspective view of a typical flowering plant of 'Gallery Renoir'. This photograph shows the colors as true as it is reasonably possible to obtain in colored reproductions of this type. Floret and foliage colors in the photograph may differ from the actual colors due to light reflectance.

In the following description, color references are made to The Royal Horticultural Society Colour Chart except where general terms of ordinary dictionary significance are used. The following observations and measurements describe plants grown in Lisse, The Netherlands, under conditions which approximate those generally used in commercial potted Dahlia production with day temperatures averaging 21° C and night temperatures averaging 14° C. Plants were grown during the summer and measurements and numerical values were averages derived from typical flowering plants in September.

Botanical classification: Dahlia hybrid cultivar 'Gallery Renoir'.

Commercial classification: Decorative potted Dahlia.

Parentage:

*Male or pollen parent.*—Dahlia hybrid cultivar 'Oriental Dream' (not patented).

*Female or seed parent.*—Dahlia hybrid cultivar 'Tout à Toi' (not patented).

Propagation:

*Type.*—Terminal tip cuttings or by tuberous divisions.

*Time to rooting.*—About 14 days with soil temperatures of 20° C.

*Rooting habit.*—Central root with numerous secondary roots that are fine and fibrous.

Plant description:

*Appearance.*—Perennial herbaceous decorative-type Dahlia, suitable as potted plants, garden or patio plants, or as cut flowers. Upright and spreading, compact habit and freely branching.

*Plant height.*—About 25 cm, appropriate for 12 to 15-cm containers.

*Growth rate.*—Rapid, typically only 65 days are required from an unrooted cutting to a finished flowering plant.

*Foliage description.*—Leaf arrangement: Opposite, simple or compound. Compound leaves have either three or five leaflets. Leaf size, single: Length: About 10 cm. Width: About 5 cm. Leaf size, compound: Length: About 18 cm. Width: About 14 cm. Leaf shape: Ovate. Leaf apex: Acute. Leaf base: Acute. Leaf margin: Finely serrate. Leaf texture: Smooth. Color: Young foliage adaxial surface: 137B. Young foliage abaxial surface: 191A. Mature foliage adaxial surface: 147A. Mature foliage abaxial surface: 191A. Venation adaxial surface: 146A. Venation abaxial surface: 147C. Petiole: Length: About 2 cm. Color: 146B.

Inflorescence description:

*Appearance.*—Fully double decorative-type inflorescence form with pink-colored ray florets. Inflorescences borne on terminals above foliage.

*Flowering response.*—Under natural conditions, plant flower from July to November in the Northern Hemisphere.

*Postproduction longevity.*—On the plant, open inflorescences will maintain good color and substance for at about 14 days. As a cut flower, open inflorescences will maintain good color and substance for at least 6 days. Plants will continue to maintain good substance and flowering for three to four months.

*Quantity of inflorescences.*—Numerous, continuous flowering.

*Inflorescence size.*—Diameter: About 11 cm. Depth (height): About 1.5 cm.

*Inflorescence bud.*—Size: Length: About 8 mm. Width: About 10 mm. Rate of opening: About 14 days. Color: 151C.

*Ray florets.*—Shape: Long and narrow. Size: Length: About 4.3 cm. Width: About 1.5 cm. Apex: Pointed. Margin: Entire. Texture: Smooth, satiny. Aspect: Flat, some undulation. Color: When opening: 64A. Adaxial surface: 66D with 13A at base. Abaxial surface: 63C with 151D at base, 64A at margin. Fading: Towards light pink to white.

*Disc florets.*—Few and inconspicuous.

*Peduncle.*—Length: 10 to 15 cm. Aspect: Strong, erect. Texture: Glabrous. Color: 138C with anthocyanin.

*Sepals.*—Quantity: 7 to 8. Shape: Long, narrow, with pointed apex. Color: Adaxial surface: 144A with anthocyanin. Abaxial surface: 146A with anthocyanin.

*Reproductive organs.*—Androecium: Anther shape: Tubular and pointed. Anther length: Less than 1 mm. Anther color: 14B. Pollen color: 15A. Gynoecium: Stigma color: 14A. Style length: About 4 mm. Style color: 154B.

Disease resistance: No known Dahlia diseases observed to date on plants grown under commercial conditions.

Seed production: Seed production has not been observed.

It is claimed:

1. A new and distinct cultivar of Dahlia plant named 'Gallery Renoir', as illustrated and described.

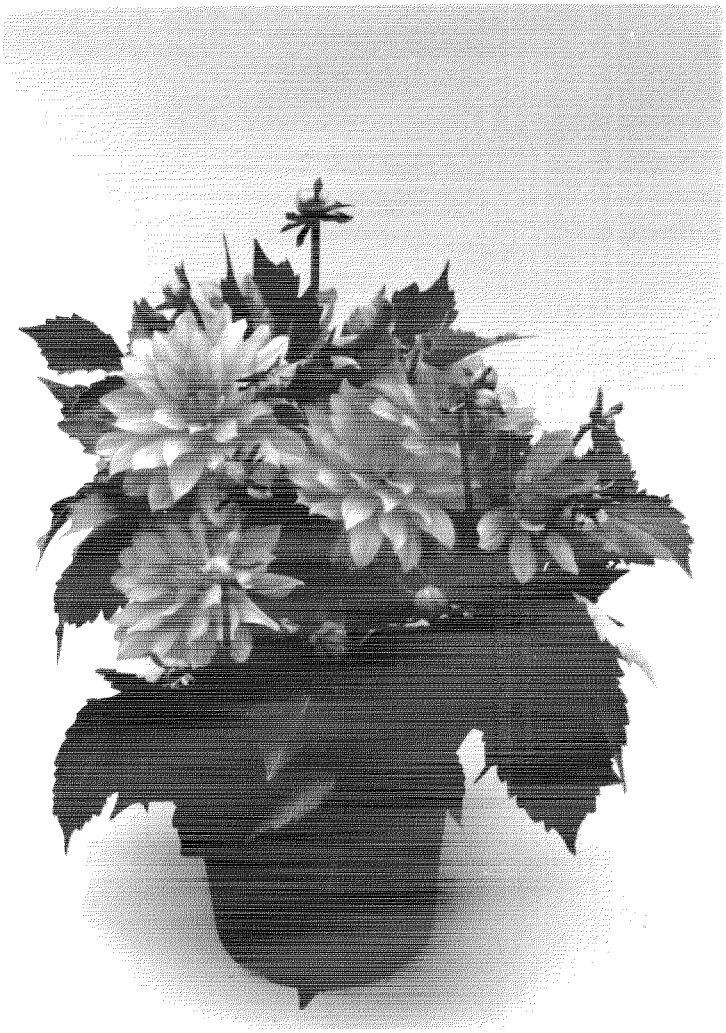

* * * * *